(12) United States Patent
Garcia et al.

(10) Patent No.: US 8,197,507 B2
(45) Date of Patent: Jun. 12, 2012

(54) SUTURELESS METHODS FOR LACERATION CLOSURE

(75) Inventors: Pablo E. Garcia, Menlo Park, CA (US); Bryan Chavez, Palo Alto, CA (US); Jomayon Hill, San Jose, CA (US)

(73) Assignee: SRI International, Menlo Park, CA (US)

( * ) Notice: Subject to any disclaimer, the term of this patent is extended or adjusted under 35 U.S.C. 154(b) by 626 days.

(21) Appl. No.: 12/353,966

(22) Filed: Jan. 14, 2009

(65) Prior Publication Data

US 2009/0182373 A1 Jul. 16, 2009

Related U.S. Application Data

(60) Provisional application No. 61/020,979, filed on Jan. 14, 2008, provisional application No. 61/142,837, filed on Jan. 6, 2009.

(51) Int. Cl.
*A61B 17/08* (2006.01)
(52) U.S. Cl. ........ 606/215; 606/213; 606/214; 424/427; 623/4.1
(58) Field of Classification Search ................... 606/151, 606/213–221; 623/4.1, 5.11–5.16, 6.11–6.64; 602/41–59, 4.1, 5.11–5.16, 6.11–6.64; 424/423, 424/427
See application file for complete search history.

(56) References Cited

U.S. PATENT DOCUMENTS

| | | | |
|---|---|---|---|
| 5,836,970 A * | 11/1998 | Pandit | 606/213 |
| 5,910,155 A | 6/1999 | Ratcliff et al. | |
| 6,124,273 A | 9/2000 | Drohan et al. | |
| 6,391,049 B1 * | 5/2002 | McNally et al. | 606/214 |
| 6,554,851 B1 * | 4/2003 | Palasis et al. | 606/213 |
| 6,589,269 B2 | 7/2003 | Zhu et al. | |
| 6,783,539 B1 * | 8/2004 | Timberlake et al. | 606/214 |
| 6,939,364 B1 * | 9/2005 | Soltz et al. | 606/214 |
| 7,073,510 B2 * | 7/2006 | Redmond et al. | 128/898 |
| 7,148,209 B2 * | 12/2006 | Hoemann et al. | 514/55 |
| 7,216,651 B2 * | 5/2007 | Argenta et al. | 128/897 |
| 7,371,403 B2 | 5/2008 | McCarthy et al. | |
| 7,381,859 B2 | 6/2008 | Hunt et al. | |
| 2003/0212387 A1 * | 11/2003 | Kurtz et al. | 606/4 |

(Continued)

OTHER PUBLICATIONS

Tissue Welding in a Porcine Eye Model Using Bovine Serum Albumin Solder and Computer-guided Laser B.H. Smith, J.Hill, K.S. Bower, P.E. Garcia, M.J. Mines, J. Menon Poster presented at: Association for Research in Vision and Ophthalmology Annual Meeting Apr. 30-May 6, 2007 in Ft. Lauderdale, Florida.

(Continued)

*Primary Examiner* — Corrine M McDermott
*Assistant Examiner* — Alexander Orkin
(74) *Attorney, Agent, or Firm* — Richard Aron Osman

(57) ABSTRACT

Tissue lacerations are closed using a vacuum cup applied to the tissue surface having a tissue-abutting, optically transparent mesh surface that under vacuum conforms with the tissue surface, apposing edges of the wound, and is optionally loaded with a bandage comprising a chitosan film and a collagen backing. An eye tissue surface wound is closed without sutures by closing the wound with a bioadhesive, biocompatible sclera or cornea wound patch comprising a chitosan film and a collagen backing, wherein the backing is bonded to the film without adhesive and protects the film against dissociation when the patch is exposed to a physiological fluid, and the film adheres to the sclera sufficient to retain apposed edges of the wound.

20 Claims, 2 Drawing Sheets

U.S. PATENT DOCUMENTS

| | | | |
|---|---|---|---|
| 2005/0004599 A1* | 1/2005 | McNally-Heintzelman et al. | 606/214 |
| 2006/0173470 A1* | 8/2006 | Oray et al. | 606/151 |
| 2006/0276846 A1* | 12/2006 | Malecki et al. | 607/2 |
| 2008/0103489 A1* | 5/2008 | Dahners | 604/543 |
| 2008/0260794 A1* | 10/2008 | Lauritzen et al. | 424/423 |
| 2009/0143818 A1* | 6/2009 | Faller et al. | 606/216 |

OTHER PUBLICATIONS

Chitosan Bandage Closure of Scleral Lacerations in a Porcine Eye Model M.J. Mines, P.E. Garcia, J.Hill, K.S. Bower, J. Menon, M. Ho, B. Chavez Poster presented at: Association for Research in Vision and Ophthalmology Annual Meeting Apr. 30-May 6, 2007 in Ft. Lauderdale, Florida.

* cited by examiner

SUTURELESS METHODS FOR LACERATION CLOSURE

This application claims priority to U.S. Ser. No. 61/020,979, filed Jan. 14, 2008, and U.S. Ser. No. 61/142,837, filed Jan. 6, 2009, both by the same inventors.

This work was funded in part by US Army Medical Research and Materiel Command, Telemedicine and Advanced Technology Research Center Contract Number W81XWH-05-C-0117; the Government has certain rights in this invention.

FIELD OF THE INVENTION

The field of the invention is sutureless methods for laceration closure.

BACKGROUND OF THE INVENTION

Trauma to the cornea and sclera is common, but current suturing techniques present limitations. In the case of lacerations that extend to the posterior part of the eye, surgeons have no choice but to leave the wounds open because of difficulty in accessing and closing them with sutures. In other cases, injuries may involve loss of tissue due to avulsion or necrosis, leaving insufficient tissue to effect a suture repair. Likewise, in modern cataract surgery where sutures are often not used the risk of infection remains. [1] A less intrusive technique than suturing might enable such wounds to be closed, thereby improving surgical outcomes. At present there are few alternatives to suture closure of scleral defects, and each has drawbacks. While cyanoacrylate glue has been used, problems such as ease and uniformity of application exist. [2, 3] Fibrin glues suffer from poor tensile strength. [2] Laser tissue welding uses laser energy to cure solder commonly composed of albumin, but its application remains limited due to the lack of consistency in the outcomes, solubility in physiologic fluids, and thermal damage to the underlying tissue. [2] Some promising laser tissue welding research has been performed using biodegradable polymer films [4] and recently using chitosan. [5] Using films instead of solders may make tissue manipulation easier and take less time to complete the laceration closure.

Portions of this material were presented at the Medicine Meets Virtual Reality Conference, Feb. 6-9, 2007, Long Beach Calif., and as posters at the Association for Research in Vision and Opthalmology Annual Meeting Apr. 30-May 6, 2007 in Ft. Lauderdale, Fla.

SUMMARY OF THE INVENTION

The invention provides methods and compositions for closing wounds.

In one embodiment, the invention provides a bioadhesive, biocompatible sclera or cornea wound patch comprising a chitosan film and a collagen backing, wherein the backing is bonded to the film without adhesive and protects the film against dissociation when the patch is exposed to a physiological fluid, and the film adheres to the sclera sufficient to retain apposed edges of the wound. In a particular embodiment the patch is a cornea patch and is optically-transparent.

The subject patches may be incorporated into a device for closing a tissue surface wound comprising: a vacuum cup comprising a mesh surface adapted to receive the tissue surface, wherein when the vacuum cup is applied to the tissue surface and placed under vacuum, the mesh and tissue surfaces conform, apposing edges of the wound, wherein the vacuum cup is adapted to transfer to the wound, and is loaded with the wound patch, to close the wound.

In another embodiment, the invention provides a device for closing a tissue surface wound comprising: a vacuum cup comprising a mesh surface adapted to receive the tissue surface, wherein when the vacuum cup is applied to the tissue surface and placed under vacuum, the mesh and tissue surfaces conform, apposing edges of the wound, wherein the vacuum cup is optically transparent to transmit laser light through the mesh to weld close the wound.

The invention encompasses methods of using the subject patches and devices to close a tissue surface wound.

In another embodiment, the invention provides a method for closing a tissue surface wound, comprising: (a) placing over the wound a mesh surface of a vacuum cup adapted to receive the tissue surface, wherein the mesh surface is further adapted to transfer to the wound, and is loaded with a bioadhesive, biocompatible tissue wound patch comprising a chitosan film and a collagen backing, wherein the backing is bonded to the film without adhesive and protects the film against dissociation when the patch is exposed to a physiological fluid, and the film adheres to the tissue surface sufficient to retain apposed edges of the wound; (b) applying a vacuum to the cup, whereby the mesh and tissue surfaces conform, apposing edges of the wound, and the patch adheres to the tissue surface over the wound to close the wound; and (c) releasing the vacuum and removing the cup from the tissue surface. In preferred embodiments, the tissue is sclera or cornea, and the patch is optically-transparent.

In another embodiment, the invention provides a method for closing a tissue surface wound, comprising: (a) placing over the wound a mesh surface of a vacuum cup adapted to receive the tissue surface, wherein the vacuum cup is optically transparent to transmit laser light through the mesh to weld close the wound; (b) applying a vacuum to the cup, whereby the mesh and tissue surfaces conform, apposing edges of the wound; (c) welding the edges of the wound with a laser to close the wound; and (d) releasing the vacuum and removing the cup from the tissue surface. In preferred embodiments, the tissue is sclera or cornea.

DETAILED DESCRIPTION OF SPECIFIC EMBODIMENTS OF THE INVENTION

Figure 1:
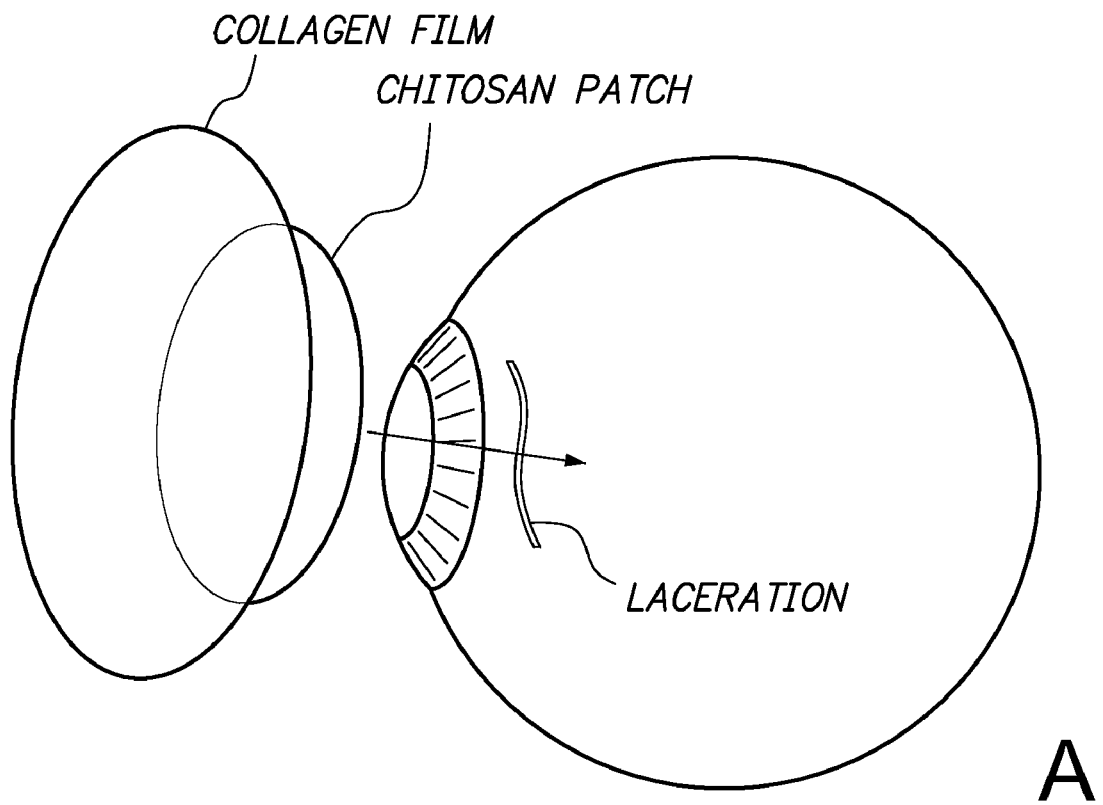
FIG. 1 shows a bioadhesive patch according to the invention: (A) perspective view; (B) cross-sectional view.
Figure 1:
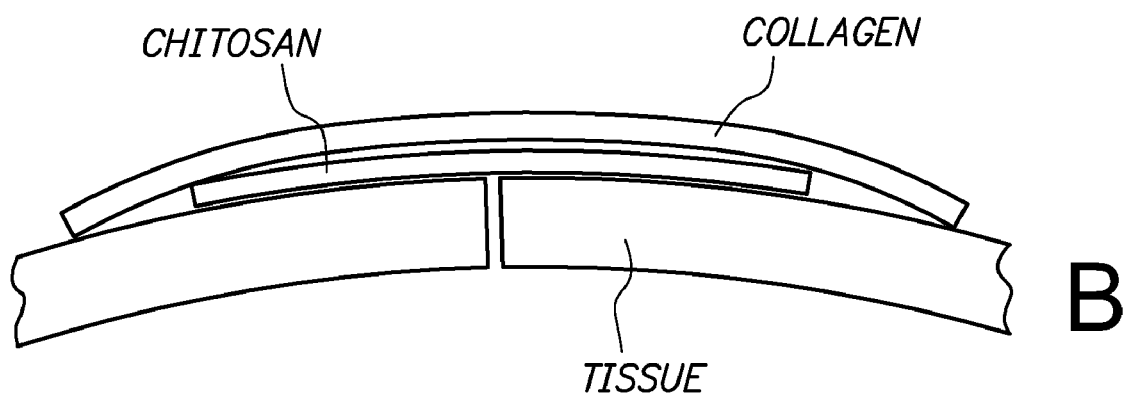
Figure 2:
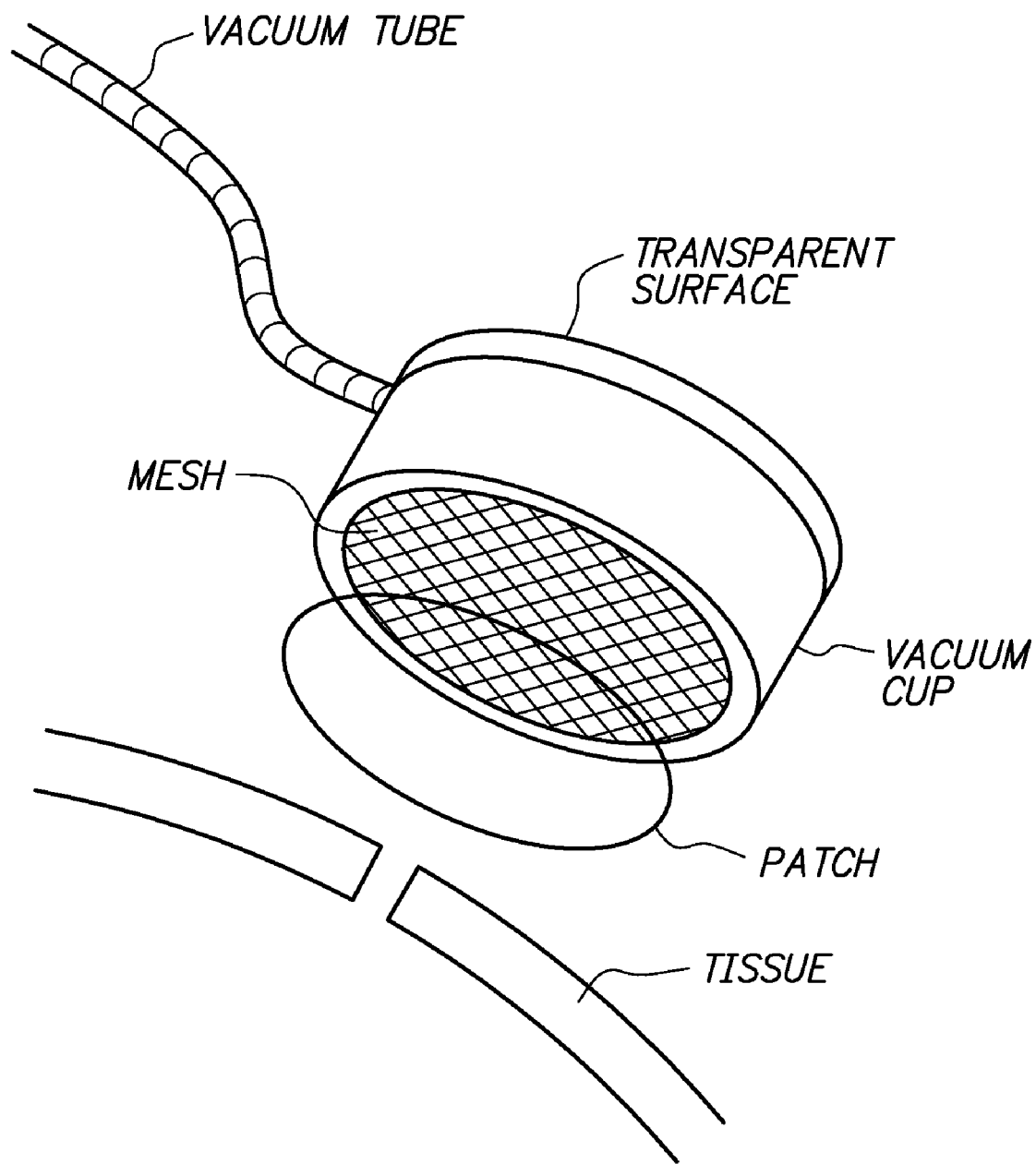
FIG. 2 shows a tissue wound closure device according to the invention.

In specific embodiments the invention provides a system for bonding tissue comprising or consisting of a bioadhesive chitosan based film which is placed over a laceration of the tissue, means of placing and pressing the film on the tissue, and means of apposing the tissue edges.

The invention encompasses alternative embodiments such as wherein a biocompatible water resistant film, such as collagen, is placed over the side of the chitosan not in contact with the tissue to prevent it from peeling off in a wet environment, or over part of the chitosan in contact with the tissue to allow closing a laceration with missing tissue.

In particular embodiments, the invention provides means for placing the film on the tissue, such as a suction cup which presses the chitosan film on the tissue, and/or means from apposing the tissue edges, such as a suction cup which presses the tissue edges together. In particular embodiments, (a) the suction cup contacts the tissue with a fine mesh through which air or low viscosity liquids can be evacuated, and/or (b) the suction cup can be deformed to bring the tissue edges together The invention provides systems for tissue bonding including:

Hand-held device embodiments to perform the following steps: (a) appose tissue, e.g. using a vacuum cup; (b) apply a chitosan film; and (c) apply a biocompatible hydrophobic film backing the chitosan, such as collagen.

System to perform robotic laser tissue welding embodiments including:

solder, film or mesh applicator which apposes and holds tissue and/or presses film against tissue, and may incorporate system embodiments that use compliant transparent surface to maintain pressure between tissue and film or mesh and/or system embodiments that use a suction cup with a transparent surface to press on tissue, particularly transparent to NIR to allow lasering tissue while maintaining pressure between tissue edges or between tissue and film; and create vacuum on heated area to allow fast curing of solder;

laser scanner, which may be (a) incorporated into a laparoscopic device, (b) separate from camera, and/or capable of raster, grid or spot welding patterns (alternate for temperature control of tissue); and planning software, wherein a laser trajectory is adapted to be the same from the point of view of the camera, and/or calibration is performed by recognizing the laser spot with a vision algorithm.

Robotic laser tissue welding embodiments: using a robotic manipulator to appose and hold tissue during laser tissue welding; and/or controlling the delivery of energy with an automated system.

Chitosan applicator embodiments: (a) chitosan patch backed by a hydrophobic film; (b) device to apply film by using vacuum cup; (c) device to appose tissue using vacuum; and/or computer controlled scanning of laser over film with various welding patterns such as raster, grid and spots.

Soldering (BSA) embodiments, including (a) performing soldering under vacuum; and/or (b) performing soldering with a mesh under vacuum.

EXAMPLE

Tissue Welding in a Porcine Eye Model Using Bovine Serum Albumin Solder, Computer-Guided Laser and Transparent Vacuum Cup Robotic surgery currently uses suturing techniques that are very challenging for a tele-operated robot, especially when done remotely with time delays. In an effort to combine robotics and laser tissue welding to increase the ease of surgery and the consistency of bonds, this study was to designed demonstrate the feasibility of scleral wound closure using bovine serum albumin (BSA) solder and computer-guided laser in a porcine eye model.

A 5-mm full-thickness radial scleral laceration was created 5-mm posterior to the limbus in enucleated whole porcine globes using a 15 degree scalpel. In 6 eyes the BSA solder (40% BSA, 0.5% hyaluronic acid, 59.5% water) was brought to room temperature and a thin layer brushed over the laceration. Enhanced efficacy is achieved by apposing the wound edges using a transparent suction cup device having a conforming, tissue-abutting mesh. Laser irradiation was performed using an near infrared laser (1455 nm) in a raster pattern (20 mm/sec) perpendicular to the incision with a power level of 350-450 mW for 3 minutes. Laser delivery is optionally computer controlled. The solder application/laser cure was repeated twice more. Three eyes were closed by hand with 10-0 nylon suture for comparison. Time to closure and leak pressure were determined for each eye. The leak pressure was measured by slowly infusing normal saline into the eye via an 18-gauge needle passed through the posterior sclera near the optic nerve. A pressure transducer attached to the tubing monitored intraocular pressure. Three of the BSA soldered eyes and the sutured eyes were measured immediately after wound closure. The other 3 BSA soldered eyes were kept moist in a paper based dressing soaked in a saline solution and refrigerated for 24 hours prior to pressurization.

Laser tissue welding with a BSA solder and computer-guided laser pattern successfully closed scleral lacerations with leak pressure exceeding that of sutured wounds immediately after wound closure. Although the solder strength degraded approximately 50% by 24 hours after treatment, the wounds remained closed with leak pressure well above physiologic pressures.

EXAMPLE

Robotic Laser Tissue Welding of Sclera Using Chitosan Films

In this study we evaluated scleral wound closure using chitosan film with and without the application of near-infrared laser irradiation using a robotic manipulator and a laser scanner. We incorporated the laser tissue welding into a surgical robotic platform in an attempt to provide greater control over some of the parameters that are critical for a successful outcome of the bonds, such as the scanning uniformity and consistency of the energy delivery.

The experiments were performed on porcine eyeballs with radial lacerations in the sclera. To compare the different methods, we evaluated their ability to effect a watertight closure, measured leak pressures and times to complete the closures using manual microsuturing as a baseline.

Preparation of Chitosan Film: In a series of preliminary experiments we explored several previously reported methods to produce the chitosan films:

Method 1: Cast Chitosan dissolved in Acetic Acid. 85% de-acetylated chitosan (2%) (Practical Grade Sigma-Aldrich, USA) was dissolved in acetic acid (2%) (JT Baker, USA) and water. The mixture was cast as a film by pouring it on a flat mold 2 mm deep and left to dry in an oven at 60 degrees C. The resulting film was transparent and had a thickness in the range of 30 µm. This is the method that was ultimately used in the eye ball experiments. [6]

Method 2: Cast Chitosan dissolved in Lactic Acid. 85% de-acetylated chitosan (2%) (Practical Grade Sigma-Aldrich, USA) was dissolved in lactic acid (2%) (JT Baker, USA) and water. The mixture was cast as a film by pouring it on a flat mold 2 mm deep and left to dry in an oven at 60 degrees C. The resulting film was transparent with a yellow tint and had a thickness in the range of 30 µm. The film was more elastic than the film produced with Method 1, especially when the film came in contact with water, and had the unwanted property of peeling more easily. [6]

Method 3: Freeze dried chitosan dissolved in acetic acid. 85% de-acetylated chitosan (2%) (Practical Grade Sigma-Aldrich, USA) was dissolved in acetic acid (2%) (JT Baker, USA) and water. The mixture was cast as a film by pouring it on a flat mold 2 mm, frozen at −80 C. and lyophilized. The resulting film was compressed to 0.5 mm to form a white opaque film. Since the film was thicker than the previous methods it was more difficult to place over the globe of the eye and it was difficult to control local burning of the film during the laser exposure.

We selected cast chitosan dissolved in acetic acid (Method 1 above) for the eye experiments since it provided the most consistent strengths and was easier to place over globe lacerations.

Laser Delivery System: A Raman single mode fiber laser with a wavelength of 1455 nm laser was selected (IPG Photonics, Oxford, Mass., USA) because water presents an absorption peak at this wave length and it has been successfully used in several studies to bond tissue without a die. [6, 7] A stage was developed to handle the tissue on a flat surface with clamps and a way to measure the apposition force. A 2-D scanning system was designed and fabricated based on a galvanometer (VM500 from GSI Lumonics, Rugby, Warwickshire, UK). The scanner includes a visible red light aligned with the infrared laser beam. An optical zoom allowed modifying the size of the spot from 100 µm to 500 µm. The necessary interface to integrate the laser scanner with the robotic system was also designed. The scanner was placed between the robot arms and behind the optical microscope. The laser beam optical path is confocal with the microscope to facilitate alignment of the laser path with the optical field.

Software to control the scanner with different treatment algorithms allowed setting the laser parameters and selecting different scanning algorithms. It also allowed the surgeon to visualize an overlay of the laser path on the video image.

Determination of Optimal Laser Scanning Pattern and Energy: The laser energy can be delivered through a variety of scanning patterns to the globe. In a raster scan, the laser is scanned across the laceration at equally spaced intervals. This scan produces strong bonds across the laceration, but tends to deform the tissue because of unequal heating over the length the laceration. In a tracing pattern, the laser is scanned parallel to the laceration alternating at either side of it. This scan heats more uniformly but causes weaker bonds due to the direction in which the film tends to cure—along the laceration rather than across it. In a spot pattern, the laser is activated at discrete spots with high power and low duration along the laceration in a raster or trace pattern. This scan is intended to limit the heat-affected zone from the laser. The experiments described here were performed using a combination of raster scanning and a tracing pattern over the laceration because it produced stronger bonds in our preliminary trials. The laser energy level was varied during optimization between 350 mW and 450 mW.

Laser Parameter Selection: The laser parameters used in this study were optimized in a series of preliminary experiments by testing the bonding strength of flat strips of sclera (10 mm×10 mm) bonded by chitosan films (5 mm×15 mm). These parameters included laser power, separation of raster lines, speed of rastering and rastering time. The laser was rastered perpendicular to the laceration, with a separation of 0.5 mm between each raster line, a width of 4.5 mm at a speed of 10 mm/sec. The bonding strength was measured with a load cell by pulling on the sclera strips on each side of the laceration. The mean pulling force in the samples was 0.96N with a standard deviation of 0.3N (n=10). The primary failure mode was peeling of the films from the sclera strips.

The tissue temperature was monitored during these preliminary experiments using a thermocouple placed between the tissue and the chitosan film, to ensure it did not exceed 63 C. The laser power was further adjusted to avoid tissue shrinkage and decoloration of the tissue along the laser path while maintaining the bond strength. Once the laser settings were selected, the tissue temperature profile remained very consistent throughout the experiments, validating the hypothesis that robotic control of the laser beam would maintain the consistency of the energy delivery to the tissue.

Experimental Design: Enucleated porcine globes were used for all experiments. A vertical, full-thickness scleral laceration was created using a 15 degree blade. The wound was radial to and extended posteriorly from the equator for a total length of 5 mm. Calipers were used to confirm the dimensions of the wound before closure. Wounds were closed using one of three techniques: chitosan film without laser, chitosan film treated with laser, and suture closure. Surgical technique for each method is described below.

Non-Lasered Chitosan Films. After drying the wound with methylcellulose sponges, a 7×7 mm chitosan film was placed over the laceration and tamped into place with a dry sponge to remove fluid and air from between the film and the eye and maximize the surface area contact of the film. After ensuring adhesion, the chitosan film was covered with a collagen shield (SOFTSHIELD® 12-Hour collagen shield, Oasis, Glendora, Calif., USA) to complete the closure.

Lasered Chitosan Film: Chitosan film was placed over the laceration as described above. The film was then exposed to laser irradiation in two directions. First the laser was scanned perpendicularly (raster pattern) across the laceration for three minutes; this was followed by scanning in a direction parallel to the laceration (tracing pattern) for three minutes. Each closure included a total of 6 minutes of laser time per eye. The chitosan film was subsequently covered with a collagen shield.

Conventional Sutures. To serve as a standard against which to compare the two chitosan film techniques, we closed scleral lacerations using sutures. The laceration was closed by an experienced ophthalmic surgeon using 9-0 nylon sutures under an operating microscope. A total of three sutures spaced approximately 1.5 mm apart were used for each laceration.

Outcome Measures: The primary outcome measure was the ability to perform a watertight wound closure. This was done by direct inspection of the wound under the operating microscope as the eye was reformed with balanced salt solution to a pressure of approximately 25 mmHg and was assessed in all seven eyes per treatment group. To test stability of the closure, three of the eyes in each group were stored in a saline-moist environment overnight and re-evaluated for a watertight wound 24 hours after closure. These eyes were not available for leak pressure testing (see below).

Secondary outcome measures included time to complete the closure and leak pressure. Closure time for unlasered chitosan film was defined as the time it took to size, cut, and apply the chitosan film, collagen shield, and to confirm the watertight closure. Closure time for lasered chitosan films was defined as the preparation and application of the chitosan film, positioning on the laser platform, aligning and programming the treatment in the treatment software, delivering the 6 minutes of laser energy, covering the lasered film with a collagen shield, and confirming a watertight closure. For sutured eyes, closure time included the time to place the sutures, tie, trim and bury the knots, and assess for watertight closure. Closure time was measured in all seven eyes in each treatment group.

To rate the strength of the closure we measured the internal pressure required to cause a wound leak. An 18-gauge needle was placed into the globe parallel to the optical nerve and saline slowly injected until a leak was observed under an ophthalmic microscope. An electronic pressure sensor determined the pressure at which the wound first began to leak. Leak pressure measured in PSI was converted to millimeters mercury (mm Hg) using a conversion of 51.7 mm Hg per PSI. Leak pressure was measured immediately after wound closure in three eyes per group. Three eyes per group were used to test wound stability at 24 hours and were therefore not available for leak pressure testing. One repaired globe from each treatment group was fixed in formalin. After fixation the globes were processed, embedded in paraffin, sectioned, stained with hematoxylin and eosin and examined histologically.

RESULTS: All wounds were watertight for each of the closure methods. Mean closure time for unlasered chitosan film was 2.24 minutes (range 1.80 to 3.26 minutes) vs. 12.47 minutes (range 11.45 to 14.15 minutes) for lasered chitosan film vs. 4.83 minutes (range 4.03 to 7.30 minutes) for sutures. The mean leak pressure for unlasered chitosan film was 303.0 mm Hg (range 217 to 364 mm Hg, 3 eyes) vs. 454.7 mm Hg (range 152 to 721 mm Hg) for lasered chitosan film vs. 570.3 mm Hg (range 460 to 646 mm Hg) for sutures. At 24 hours, all wounds retained a watertight closure.

The standard fixation and sectioning process resulted in frequent artifactual separation of the chitosan film from the underlying tissue in both the non-lasered and lasered groups. Specimens from lasered chitosan eyes revealed minimal tissue change resulting from laser irradiation. Examination of sutures eyes showed uniform suture tracts within the scleral tissue.

DISCUSSION: Laser tissue welding is a topic of considerable interest. Savage et al [7] demonstrated in vitro welding of sclera and corneal tissues using a 1455 nm wavelength laser. No solder or dyes were used in the published experiments and the strengths of the welds were very high, in the order of 2 kg/cm2. Welding of tissue using albumin solders has been demonstrated by several researchers [e.g., 8]. Some of the results include very high tensile strength results, such as the work from Chan et al. [9]. Previous work published in the literature use a combination of 25% albumin, 0.5% hyaluronate and indocyanine green (ICG) with an 808 nm laser. Tissue shrinkage and thermal damage can limit results.

Chitosan has several intriguing properties that make it potentially useful as an ocular tissue adhesive. Chitosan has been shown to be biocompatible and to promote healing [10]. The corneal surface demonstrates excellent tolerance to differing formulations of topically applied chitosan. [11] Chitosan nanoparticles can be impregnated with various substances to allow drug delivery without decreasing conjunctival cell viability. [12] This suggests the possibility of incorporating antibiotic preparations within the film substrate, providing anti-bacterial activity at the wound site. In addition, chitosan appears to itself exhibit antimicrobial properties. [13] Depending on the method of preparation, chitosan also displays inherent muco-adhesive characteristics, potentially promoting initial adherence to the surgical site, facilitating closure. [14]

In this study we compared robotically controlled laser heating of chitosan films to non-lasered chitosan closure. Both robotically controlled lasered and non-lasered chitosan film resulted in watertight closures immediately and when tested after 24 hours. Despite variation in measured leak pressures, even the lowest for all types of closures exceeded IOP by a factor of 6 or greater. Lasered chitosan films resulted in higher leak pressures comparable to suture closure. Non-lasered chitosan film also resulted in high leak pressures. This study shows that sclera sealed with chitosan alone or with chitosan followed by laser apparently resulted in tissue bonding sufficient to provide an immediate watertight seal and adequate IOP.

References

[1] Kehdi E E, Watson S L, Francis I C, Chong R, Bank A, Coroneo M T, Dart J K. Spectrum of clear corneal incision cataract wound infection. J Cataract Refract Surg 2005; 31(9): 1702-6.

[2] Lauto A, Mawad D, Foster L J R. Adhesive Biomaterials for Tissue Reconstruction. J Chem Tech Biotech (2007); (Release on line: Aug. 7, 2007, DOI: 10.1002/jctb.1771).

[3] Vote B J, Elder M J. Cyanoacrylate glue for corneal perforations: a description of a surgical technique and a review of the literature. Clin Experiment Opthalmol. 2000 December; 28(6):437-42.

[4] Sorg B S, Welch A J. Tissue welding with biodegradable polymer films-demonstration of acute strength reinforcement in vivo. Lasers Surg Med 2002; 31(5):339-42.

[5] Lauto A, Stoodley M, Marcel H, Avolio A, Sarris M, McKenzie G, Sampson D D, Foster L J. In vitro and in vivo tissue repair with laser-activated chitosan adhesive. Lasers Surg Med 2007 January; 39(1): 19-27.

[6] Khan T A, Peh K K. Mechanical, bioadhesive strength and biological evaluations of chitosan films for wound dressing. J Pharm Pharmaceut Sci 2000; 3(3):303-311.

[7] Savage H E, Halder R K, Kartazayeu U, Rosen R B, Gayen T, McCormick S A, Patel N S, Katz A, Perry H D, Paul M, Alfano R R. NIR laser tissue welding of in vitro porcine cornea and sclera tissue. Lasers Surg Med. 2004; 35(4):293-303.

[8] Eaton A M, Bass L S, Libutti S K, Schubert H D, Treat M. Sutureless cataract incision closure using laser activated tissue glues. Proc of SPIE Vol 1423 Ophthalmic Technologies (1991):52-57.

[9] Chan E K, Lu Q, Bell B, Motamedi M, Frederickson C, Brown D T, Kovach I S, Welch A J. Laser assisted soldering: microdroplet accumulation with a microjet device. Lasers Surg Med. 1998; 23(4):213-20.

[10] Stone C A, Wright H, Clarke T, Powell R, Devaraj V S. Healing at skin graft donor sites dressed with chitosan. Br J Plast Surg. 2000 October; 53(7):601-6.

[11] Felt O, Furrer P, Mayer J M, Plazonnet B, Buri P, Gurny R. Topical use of chitosan in opthalmology: tolerance assessment and evaluation of precorneal retention. Int J. Pharm. 1999 Apr. 15; 180(2): 185-93.

[12] de Campos A M, Diebold Y, Carvalho E L, Sánchez A, Alonso M J. Chitosan nanoparticles as new ocular drug delivery systems: in vitro stability, in vivo fate, and cellular toxicity. Pharm Res. 2004 May; 21(5):803-10.

[13] Felt O, Carrel A, Baehni P, Buri P, Gurny R. Chitosan as tear substitute: a wetting agent endowed with antimicrobial efficacy. J Ocul Pharmacol Ther. 2000 June; 16(3):261-70.

[14] Lauto A, Hook J, Doran M, Camacho F, Poole-Warren L A, Avolio A, Foster L J. Chitosan adhesive for laser tissue repair: in vitro characterization. Lasers Surg Med. 2005 March; 36(3): 193-201.

[15] Wright N, Humphrey J. Denaturation of collagen via heating: an irreversible rate process. Annu Rev Biomed Eng. 2002 March; 4: 109-128.

The descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A sutureless method for closing an eye tissue surface wound, comprising step(s):
    closing the wound with a bioadhesive, biocompatible sclera or cornea wound patch comprising a chitosan film and a collagen backing, wherein the backing is bonded to the film without adhesive and protects the film against dissociation when the patch is exposed to a physiological fluid, and the film adheres to the tissue sufficient to retain apposed edges of the wound, wherein the closing step (a) comprises placing the film over the wound, tamping the film into place to remove fluid or air from between the film and the wound, and then covering the film with the backing; (b) is non-lasered; or (c) comprises lasering the film to the eye.

2. The method of claim 1 wherein the closing step comprises placing the film over the wound, tamping the film into place to remove fluid or air from between the film and the wound, and then covering the film with the backing.

3. The method of claim 1 wherein the chitosan film is a dried cast of acetic acid dissolved chitosan.

4. The method of claim 1 wherein the closing step is non-lasered.

5. The method of claim 1 wherein the closing step comprises placing the film over the wound, tamping the film into place to remove fluid or air from between the film and the wound, and then covering the film with the backing, wherein the chitosan film is a dried cast of acetic acid disolved chitosan, wherein the patch is a cornea patch and is optically-transparent, and wherein the closing step is non-lasered.

6. The method of claim 1 wherein the closing step comprises lasering the film to the eye.

7. The method of claim 1 wherein the closing step comprises lasering the film to the eye by scanning a laser both perpendicularly across (a raster pattern) and parallel to (a tracing pattern) the wound.

8. The method of claim 1 wherein the patch is delivered to the tissue with a device comprising:
    a vacuum cup comprising a mesh surface adapted to receive the tissue surface, wherein when the vacuum cup is applied to the tissue surface and placed under vacuum, the mesh and tissue surfaces conform, apposing edges of the wound to close the wound, wherein the vacuum cup is adapted to transfer to the wound, and is loaded with the wound patch.

9. The method of claim 1 wherein the patch is delivered to the tissue with a device comprising:
    a vacuum cup comprising a mesh surface adapted to receive the tissue surface, wherein when the vacuum cup is applied to the tissue surface and placed under vacuum, the mesh and tissue surfaces conform, apposing edges of the wound to close the wound, wherein the vacuum cup is adapted to transfer to the wound, and is loaded with the wound patch; and
    wherein the closing step comprises lasering the film to the eye.

10. A sutureless method for closing an eye tissue surface wound, comprising step(s):
    closing the wound with a bioadhesive, biocompatible sclera or cornea wound patch comprising a chitosan film and a collagen backing, wherein the backing is bonded to the film without adhesive and protects the film against dissociation when the patch is exposed to a physiological fluid, and the film adheres to the tissue sufficient to retain apposed edges of the wound, wherein the patch is a cornea patch and is optically-transparent.

11. A sutureless method of using, for closing an eye tissue surface wound, a bioadhesive, biocompatible sclera or cornea wound patch comprising a chitosan film and a collagen backing, wherein the backing is bonded to the film without adhesive and protects the film against dissociation when the patch is exposed to a physiological fluid, and the film adheres to the tissue sufficient to retain apposed edges of the wound, the method comprising steps:
    placing over the wound a mesh surface of a vacuum cup adapted to receive the tissue surface, wherein the mesh surface is further adapted to transfer to the wound, and is loaded with the patch;
    applying a vacuum to the cup, whereby the mesh and tissue surfaces conform, apposing edges of the wound, and the patch adheres to the tissue surface over the wound to close the wound; and
    releasing the vacuum and removing the cup from the tissue surface.

12. The method of claim 11 wherein the tissue is cornea and the patch is optically-transparent.

13. The method of claim 11 wherein the closing step comprises placing the film over the wound, tamping the film into place to remove fluid or air from between the film and the wound, and then covering the film with the backing.

14. The method of claim 11 wherein the chitosan film is a dried cast of acetic acid dissolved chitosan.

15. The method of claim 11 wherein the patch is a cornea patch and is optically-transparent.

16. The method of claim 11 wherein the closing step is non-lasered.

17. The method of claim 11 wherein the closing step comprises placing the film over the wound, tamping the film into place to remove fluid or air from between the film and the wound, and then covering the film with the backing, wherein the chitosan film is a dried cast of acetic acid disolved chitosan, wherein the patch is a cornea patch and is optically-transparent, and wherein the closing step is non-lasered.

18. The method of claim 11 wherein the closing step comprises lasering the film to the eye.

19. The method of claim 11 wherein the closing step comprises lasering the film to the eye by scanning a laser both perpendicularly across (a raster pattern) and parallel to (a tracing pattern) the wound.

20. The method of claim 11 comprising a subsequent step of confirming a resultant water tight closure of the wound.

* * * * *